United States Patent
Arnz et al.

(10) Patent No.: US 9,377,415 B2
(45) Date of Patent: Jun. 28, 2016

(54) MEASURING DEVICE FOR MEASURING AN ILLUMINATION PROPERTY

(71) Applicant: Carl Zeiss SMT GmbH, Oberkochen (DE)

(72) Inventors: Michael Arnz, Oberkochen (DE); Markus Deguenther, Aalen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 14/501,220

(22) Filed: Sep. 30, 2014

(65) Prior Publication Data
US 2015/0015875 A1 Jan. 15, 2015

Related U.S. Application Data

(63) Continuation of application No. PCT/EP2013/000850, filed on Mar. 21, 2013.

(60) Provisional application No. 61/618,345, filed on Mar. 30, 2012.

(30) Foreign Application Priority Data

Mar. 30, 2012 (DE) .......................... 10 2012 205 181

(51) Int. Cl.
*G01N 21/95* (2006.01)
*G01J 1/00* (2006.01)
(Continued)

(52) U.S. Cl.
CPC . *G01N 21/95* (2013.01); *G01J 1/00* (2013.01); *G01J 1/429* (2013.01); *G01J 1/4257* (2013.01); *G01N 21/8806* (2013.01); *G01N 21/9501* (2013.01); *G03F 1/84* (2013.01)

(58) Field of Classification Search
USPC .............. 356/124, 124.5, 126–127, 317–318; 355/67, 77; 250/372
See application file for complete search history.

(56) References Cited

U.S. PATENT DOCUMENTS 5,177,774 A * 1/1993 Suckewer ................ G21K 7/00
378/43
5,706,091 A 1/1998 Shiraishi
(Continued)

FOREIGN PATENT DOCUMENTS

DE          10158921 A1    6/2003
DE        102007020033 A1    1/2008
DE        102008003916 A1    7/2008

OTHER PUBLICATIONS

International Search Report and Written Opinion in counterpart International Application No. PCT/EP2013/000850, mailed Jul. 11, 2013.
(Continued)

*Primary Examiner* — Sang Nguyen
(74) *Attorney, Agent, or Firm* — Edell, Shapiro & Finnan, LLC

(57) ABSTRACT

A measuring device (40) for measuring an illumination property of an illumination system (12), which is configured for two-dimensional irradiation of a substrate (24) arranged in an illumination plane (21) with illumination radiation (20). Two differing measurement beam paths (52, 54) are formed in the measuring device, each arranged to guide the illumination radiation emitted by the illumination system onto a spatially resolving intensity detector (42) of the measuring device. A first (52) of the measurement beam paths is arranged to measure an intensity distribution in the illumination plane and the second (54) of the measurement beam paths is arranged to measure an intensity distribution in a pupil of the illumination system. The measuring device also includes an imaging optical unit (44) arranged in the first measurement beam path (52) such that the illumination radiation guided in the first measurement beam path passes through the imaging optical unit.

15 Claims, 3 Drawing Sheets

(51) Int. Cl.
  *G01J 1/42* (2006.01)
  *G01N 21/88* (2006.01)
  *G03F 1/84* (2012.01)

(56) References Cited

U.S. PATENT DOCUMENTS

| | | | |
|---|---|---|---|
| 6,954,266 B2 * | 10/2005 | Tomie | G01N 21/95623 250/492.2 |
| 7,005,649 B1 * | 2/2006 | Tezuka | G01N 21/47 250/372 |
| 7,298,498 B2 | 11/2007 | Takahashi | |
| 7,667,829 B2 | 2/2010 | Kaise et al. | |
| 2002/0113975 A1 * | 8/2002 | Komulainen | G01B 11/303 356/600 |
| 2004/0257559 A1 | 12/2004 | Dieckmann | |
| 2005/0162650 A1 * | 7/2005 | Yamamoto | G01J 3/28 356/328 |
| 2005/0274897 A1 * | 12/2005 | Singer | G03F 7/70141 250/372 |
| 2008/0019586 A1 | 1/2008 | Chen et al. | |
| 2009/0097094 A1 | 4/2009 | Tanaka | |
| 2010/0020302 A1 | 1/2010 | Freimann | |
| 2010/0208230 A1 | 8/2010 | Rath et al. | |
| 2011/0085151 A1 * | 4/2011 | Deguenther | G03F 7/702 355/67 |
| 2012/0075606 A1 * | 3/2012 | Nelson | G03F 1/84 355/67 |
| 2013/0132037 A1 * | 5/2013 | Kempter | G03F 7/70116 702/189 |
| 2015/0009492 A1 * | 1/2015 | Frese | G01M 11/005 356/124 |

OTHER PUBLICATIONS

Office Action in corresponding German Application No. 10 2012 205 181.3, dated Jan. 25, 2013, along with an English translation.

* cited by examiner

MEASURING DEVICE FOR MEASURING AN ILLUMINATION PROPERTY

This is a Continuation of International Application PCT/2013/000850, with an international filing date of Mar. 21, 2013, which was published under PCT Article 21(2) in English, and the complete disclosure of which is incorporated into this application by reference. This Application claims priority to German Patent Application No. 10 2012 205 181.3 filed on Mar. 30, 2012 and to U.S. Provisional Application No. 61/618,345, also filed on Mar. 30, 2012. The entire disclosures of this German Patent Application and this U.S. Provisional Application are incorporated into the present application by reference.

FIELD OF AND BACKGROUND OF THE INVENTION

The invention relates to a measuring device for measuring an illumination property of an illumination system, which is configured for two-dimensional irradiation of a substrate, arranged in an illumination plane, with illumination radiation. The invention furthermore relates to an arrangement with such a measuring device, an inspection apparatus for inspecting a surface of a substrate and a method for measuring an illumination system of the aforementioned type.

The prior art has disclosed inspection apparatuses for inspecting masks for microlithography, so-called mask inspection apparatuses, and inspection apparatuses for inspecting exposed wafers. The aerial image of the lithography mask to be inspected is measured in a mask inspection apparatus during a mask inspection in order to identify write errors of the mask or other mask defects. To this end, a mask inspection apparatus comprises an illumination system for generating illumination radiation radiated onto the mask to be inspected, and an inspection lens for imaging the mask structures on an inspection detector.

In order to obtain very precise measurement results, it is necessary to precisely set the illumination properties of the illumination system. Thus, it is necessary to ensure that both the homogeneity of the intensity distribution in the illumination plane of the illumination system, the so-called "illumination uniformity", and the intensity distribution in the pupil of the illumination system satisfy predetermined specifications. In order to ensure this, the illumination uniformity and the intensity distribution in the pupil are firstly measured using a separate suitable measuring instrument in each case, and the illumination system is calibrated thereafter.

One option for calibration consists of individually loading the respective measuring instruments into the illumination plane. However, this requires a comparatively long period of time. If the measuring instruments are integrated into the inspection apparatus, it may be possible to save some time, but the spatial requirements for the measuring instruments in the inspection apparatus are significant. In order to ensure a high accuracy of the measurement results, a calibration of the individual measuring instruments is required in any case.

OBJECTS AND SUMMARY OF THE INVENTION

It is an object of the invention to provide a measuring device and a measuring method with which the aforementioned problems are alleviated, and, in particular, with which the respective intensity distribution measurement can be effected in both the illumination plane and the pupil of an illumination system with comparatively little effort.

By way of example, the aforementioned object can, according to the invention, be achieved by a measuring device for measuring an illumination property of an illumination system, which is configured for two-dimensional irradiation, for example in an illumination field with dimensions of approximately 0.4 mm×0.4 mm, of a substrate, arranged in an illumination plane, with illumination radiation. The measuring device comprises a spatially, e.g. two-dimensionally, resolving intensity detector and two differing measurement beam paths formed in the measuring device, each of which is arranged to guide the illumination radiation emitted by the illumination system onto the intensity detector. A first one of the measurement beam paths is configured to measure an intensity distribution in the illumination plane and the second one of the measurement beam paths is configured to measure an intensity distribution in a pupil of the illumination system. The measuring device furthermore comprises an imaging optical unit arranged in the first measurement beam path such that the illumination radiation guided in the first measurement beam path passes through the imaging optical unit.

In other words, the measuring device according to the invention combines the functions for an illumination uniformity measurement and a pupil measurement. An intensity distribution determined by such a pupil measurement corresponds to the angular distribution of the illumination radiation in at least one point of the illumination plane. In particular, the imaging optical unit is configured so that the intensity distribution of the illumination radiation from the illumination plane, and hence the illumination field, is imaged on the intensity detector such that the image of the illumination field does not outshine the detection surface of the intensity detector, in particular does not cover more than 80% of the detection surface. According to one embodiment, the imaging optical unit is configured as a magnifying optical unit.

The measuring device merely requires one intensity detector because both the measurement beam path for the illumination uniformity measurement and the measurement beam path for the pupil measurement are guided onto the same intensity detector. As a result, the measuring device can be embodied to have a compact design, as a result of which it is possible to integrate the measuring device into an inspection apparatus, with this requiring relatively little space. Integrating the measuring device into an inspection apparatus in turn renders it possible to carry out the measurements in a time-saving manner. As a result of the combined use of an intensity detector, the calibration effort for a second detector is dispensed with in any case, as a result of which the overall measuring effort is likewise reduced.

In accordance with one embodiment according to the invention, the measuring device furthermore comprises two passage openings, which are arranged to respectively guide the two differing measurement beam paths to the intensity detector. In other words, the passage openings are arranged such that the first measurement beam path connects the first passage opening to the intensity detector and the second measurement beam path connects the second one of the passage openings to the intensity detector.

In accordance with one embodiment of the invention, the measuring device is configured to measure an illumination system that has a predetermined numerical aperture (NA) and emits illumination radiation having a predetermined wavelength ($\lambda$). The passage opening associated with the second measurement beam path is at least ten times larger, in particular one hundred times larger, than the quotient ($\lambda$/NA) of the predetermined wavelength and the predetermined numerical aperture. Thus, for example, a dimension of approximately 10 μm is suitable for the passage opening when using EUV radiation as illumination radiation in conjunction with a numerical aperture of 0.2. Diffraction effects are largely precluded in the case of such dimensions.

In accordance with a further embodiment according to the invention, the passage opening associated with the first measurement beam path is larger than the passage opening associated with the second beam path. In accordance with one exemplary embodiment, the passage opening associated with the first measurement beam path is at least double the size, in particular at least ten times the size, of the passage opening associated with the second beam path. The size of a passage opening is, in particular, understood to mean a maximum extent of the opening, the diameter thereof in the case of a circular embodiment of the opening. In accordance with one embodiment of a measuring device for measuring an illumination system with a numerical aperture of 0.2 and an operating wavelength of 13.5 nm, the passage opening associated with the first measurement beam path has a maximum extent of at least 0.1 mm, for example approximately 0.4 mm, and the passage opening associated with the second measurement beam path has a maximum extent of at least 1 µm, for example approximately 10 µm.

In accordance with a further embodiment according to the invention, the second measurement beam path is configured to enable wave propagation of the illumination radiation in a region between a passage opening and the intensity detector. In accordance with one variant, the measurement beam path is configured to enable unhindered wave propagation of the illumination radiation in the aforementioned region, i.e. the region is void of any radiation-influencing components.

In accordance with a further embodiment according to the invention, the second measurement beam path comprises a Fourier optical unit. A Fourier optical unit is configured to transform a radiation distribution from angular space into positional space. In other words, the Fourier optical unit is configured to transform the angular distribution of the illumination radiation at one point in the illumination plane into a spatially resolved intensity distribution on the intensity detector.

In accordance with a further embodiment according to the invention, the imaging optical unit is configured as a magnifying optical unit with a magnification factor of at least ten, in particular at least twenty or at least thirty. This means that the intensity distribution present in the illumination plane is imaged on the detector with a magnification factor of at least ten. As a result, the homogeneity of the intensity distribution in the illumination plane can be measured with a greater accuracy.

In accordance with a further embodiment according to the invention, the measuring device is configured to measure illumination radiation in the EUV wavelength range. As a result, the measuring device can be used in an inspection device for inspecting EUV masks. A precise calibration of the illumination properties is particularly important within the scope of inspecting EUV masks.

Furthermore, an arrangement is provided according to the invention, which arrangement comprises a measuring device as per one of the above-described embodiments and a repositioning device. The repositioning device is configured to reposition the measuring device with respect to the illumination system such that the illumination radiation enters either the first measurement beam path or the second measurement beam path. By way of example, the repositioning device can be embodied as a displacing table for corresponding displacement of the measuring device from a first measurement position to a second measurement position. Furthermore, the repositioning can also be effected by tilting or rotating the measuring device.

Furthermore, an inspection apparatus is provided according to the invention, for inspecting a surface of a substrate for microlithography, which inspection apparatus comprises an illumination system for two-dimensional irradiation of the substrate with illumination radiation and comprising a measuring device as per one of the above-described embodiments.

In accordance with one embodiment according to the invention, the inspection apparatus comprises an object holder for holding the substrate to be inspected. The measuring device is arranged on the object holder, in particular integrated into the object holder. By way of example, the object holder can be the mask table of a mask inspection apparatus.

In accordance with a further embodiment according to the invention, the object holder is displaceably mounted between a first measurement position, in which the illumination radiation enters the first measurement beam path, and a second measurement position, in which the illumination radiation enters the second measurement beam path. Furthermore, the object holder is preferably mounted such that the latter can be displaced into an inspection position, in which the illumination radiation irradiates the substrate to be inspected.

In accordance with a further embodiment according to the invention, the illumination system comprises an EUV radiation source. In particular, the inspection apparatus is designed to inspect EUV masks.

Furthermore, a method is provided according to the invention, for measuring an illumination property of an illumination system, which is configured for two-dimensional irradiation of a substrate, arranged in an illumination plane, with illumination radiation. The method according to the invention includes imaging an intensity distribution of the illumination radiation in the illumination plane with an imaging optical unit onto a spatially resolving intensity detector and recording the imaged intensity distribution. The method further includes guiding the illumination radiation, which is radiation having left the illumination system, onto the intensity detector in a beam path outside the imaging optical unit such that an image of a pupil of the illumination system is generated on the intensity detector. The intensity detector, which the illumination radiation is guided onto to generate the image of a pupil of the illumination system, is also used for recording the intensity distribution of the illumination in the illumination plane. In other words, the imaged intensity distribution of the illumination radiation in the illumination plane is recorded with the same detector as the detector, on which the image of a pupil of the illumination system is generated.

The imaging the intensity distribution of the illumination radiation in the illumination plane on a spatially resolving intensity detector on the one hand and the guiding of the illumination radiation onto the intensity detector such that an image of a pupil of the illumination system is generated on the intensity detector on the other hand more particularly occur at different times. In other words, measuring the illumination uniformity and measuring the intensity distribution in the pupil does not occur simultaneously, but rather successively in any sequence. In accordance with one embodiment variant, differing measurement beam paths are used for imaging the intensity distribution of the illumination radiation in the illumination plane on a spatially resolving intensity detector on the one hand and guiding the illumination radiation onto the intensity detector such that an image of a pupil of the illumination system is generated on the intensity detector on the other hand.

The phrase "imaging an intensity distribution of the illumination radiation in the illumination plane onto a spatially resolving intensity detector" especially means that the intensity distribution is imaged onto the intensity detector without a targeted structural modification of the intensity distribution, such as a modification effected by superposition of another structure with the intensity distribution. A magnification of the intensity distribution using a magnifying optical unit is not considered such a targeted structural modification.

According to an embodiment of the invention the limitations of the measuring method, i.e. recording the imaged intensity distribution of the illumination radiation in the illumination plane and generating an image of the pupil of the illumination system on the intensity detector, are performed using a single measuring device, which contains the imaging optical unit and the intensity detector.

According to a further embodiment of the invention the measuring device comprises two differing measurement beam paths, comprising a first measurement beam path, which extends through the imaging optical unit and serves for measuring the intensity distribution in the illumination plane, and a second measurement beam path, along which the illumination radiation is guided onto the intensity detector for generating an image of a pupil of the illumination system on the intensity detector.

According to a further embodiment of the invention the measuring method is performed using a measuring device having two passage openings. According to a variant of the embodiment the illumination radiation is guided through a first one of the passage openings when imaging the intensity distribution of illumination radiation in illumination plane onto the intensity detector. The illumination radiation is guided through the second passage opening when guiding the illumination radiation onto the intensity detector such that an image of a pupil of the illumination system is generated on the intensity detector.

In accordance with embodiments according to the invention, the method according to the invention is carried out using the measuring device as per one of the above-described embodiments or using the arrangement or the inspection apparatus as per one of the above-described embodiments.

The features specified in respect of the above-described embodiments, exemplary embodiments or embodiment variants of the measuring device according to the invention or the inspection apparatus according to the invention can be correspondingly transferred to the method according to the invention, and vice versa. These and other features of the embodiments, exemplary embodiments or embodiment variants according to the invention are explained in the claims and the description of the figures. The individual features can be implemented as embodiments of the invention, either separately or in combination. Furthermore, they can describe advantageous embodiments which are independently protectable and protection for which is claimed, if appropriate, first during or after pendency of the application.

BRIEF DESCRIPTION OF THE DRAWINGS

The above and further advantageous features of the invention are illustrated in the following detailed description of exemplary embodiments according to the invention with reference to the accompanying schematic drawings, in which.

DETAILED DESCRIPTION OF EXEMPLARY EMBODIMENTS

In the exemplary embodiments or embodiments described below, elements which are functionally or structurally similar to one another are as far as possible provided with the same or similar reference signs. Therefore, for understanding the features of the individual elements of a specific exemplary embodiment, reference should be made to the description of other exemplary embodiments or the general description of the invention.

Figure 1:
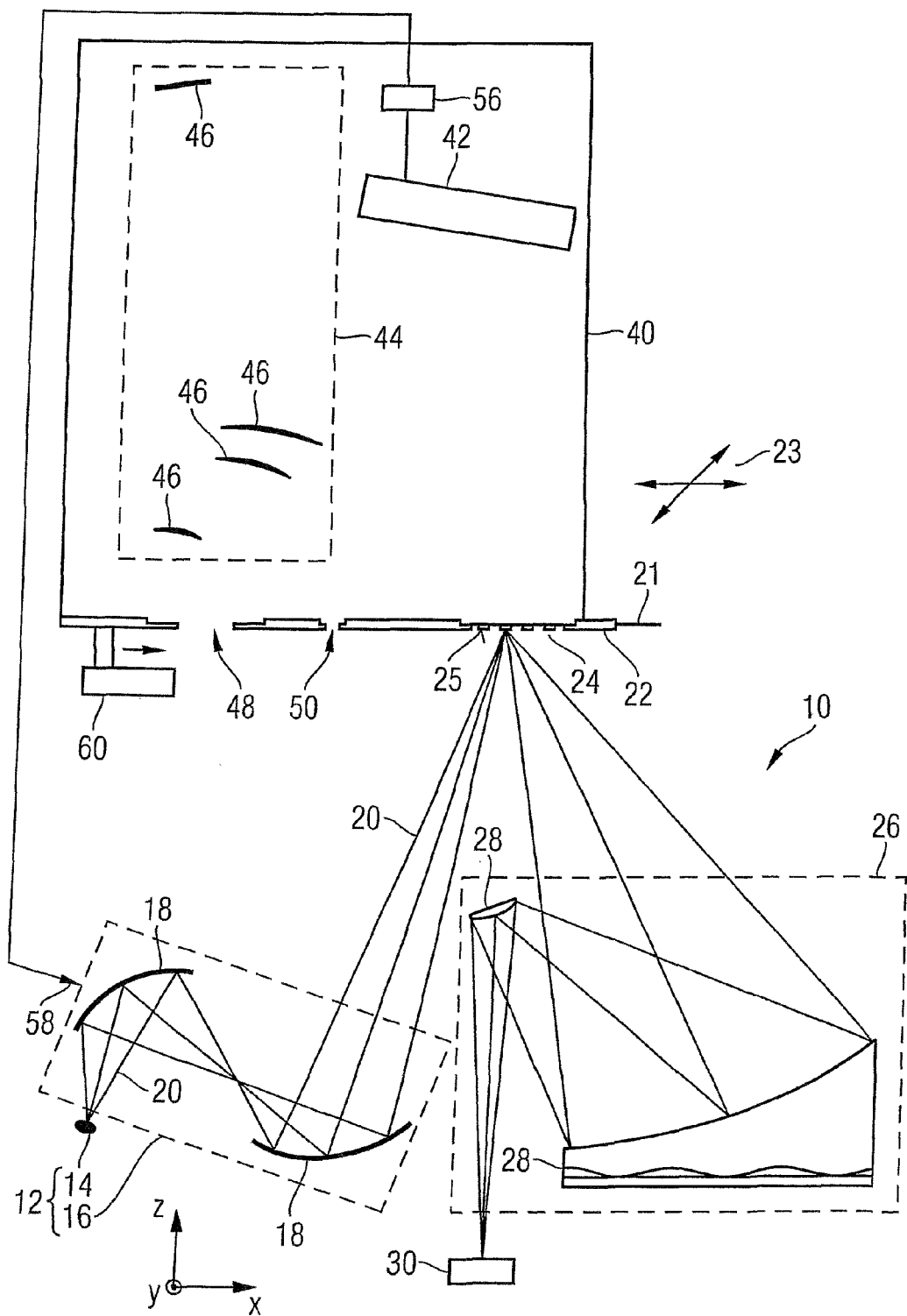
FIG. 1 shows an exemplary embodiment according to the invention of an inspection apparatus with an illumination system for illuminating a surface of a substrate to be inspected, and of a measuring device in an inspection position.

To facilitate the description, a Cartesian xyz-coordinate system is indicated in the drawing, which system reveals the respective positional relationship of the components illustrated in the figures. In FIG. 1, the y-direction runs perpendicularly to the plane of the drawing out of the latter, the x-direction runs toward the right and the z-direction runs upward.

FIG. 1 illustrates an exemplary embodiment according to the invention of an inspection apparatus 10 for inspecting a surface 25 of a substrate 24 to be inspected. In the present case, the substrate 24 to be inspected is a product mask for EUV microlithography, which is operated in reflection. This present inspection apparatus 10 therefore is a mask inspection apparatus. However, inspection apparatuses within the scope of this application can also be embodied as wafer inspection apparatuses, for example.

Figure 2:
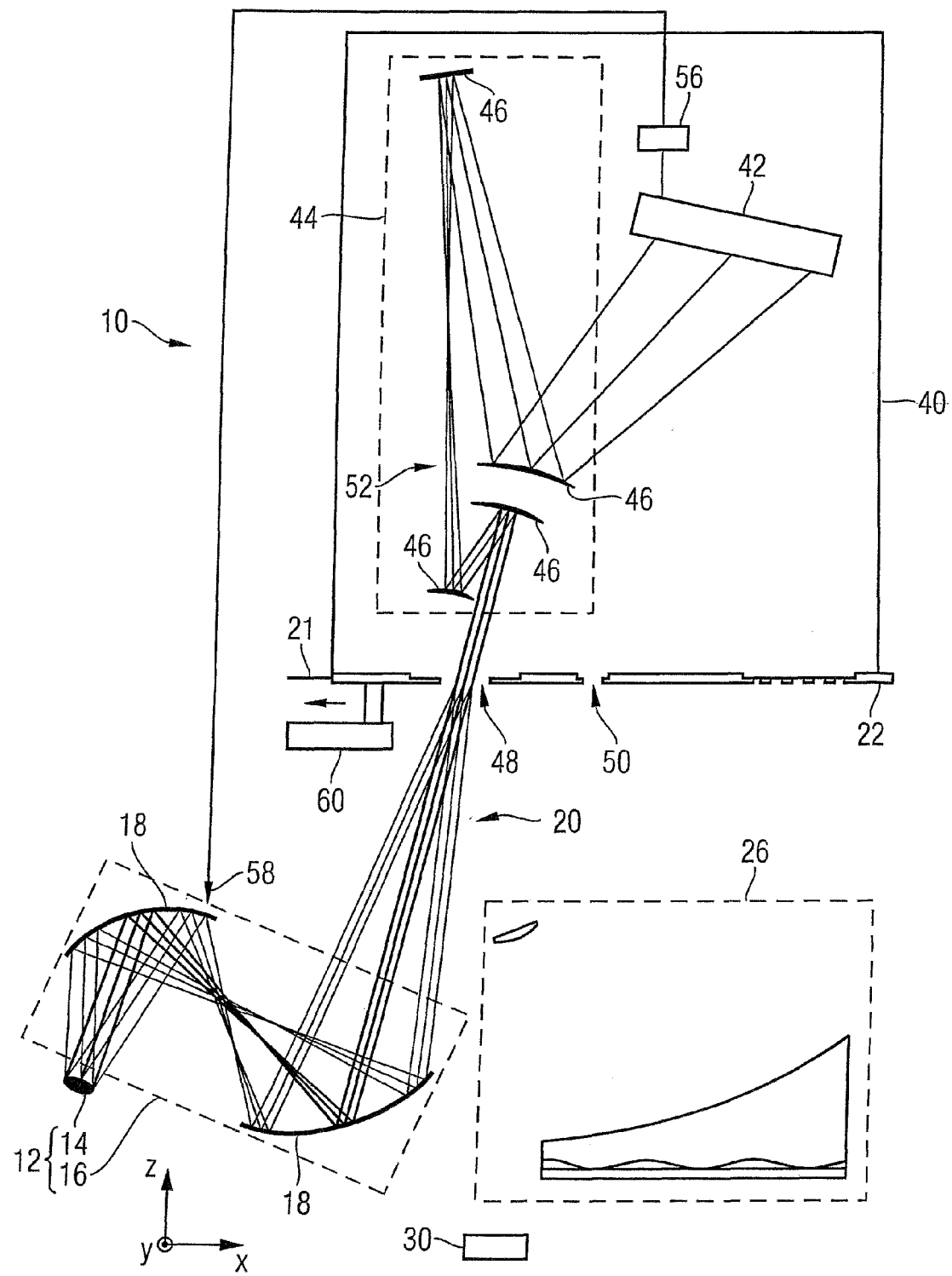
FIG. 2 shows the inspection apparatus as per FIG. 1 in a first measurement position for measuring an intensity distribution in an illumination plane of the illumination system.
Figure 3:
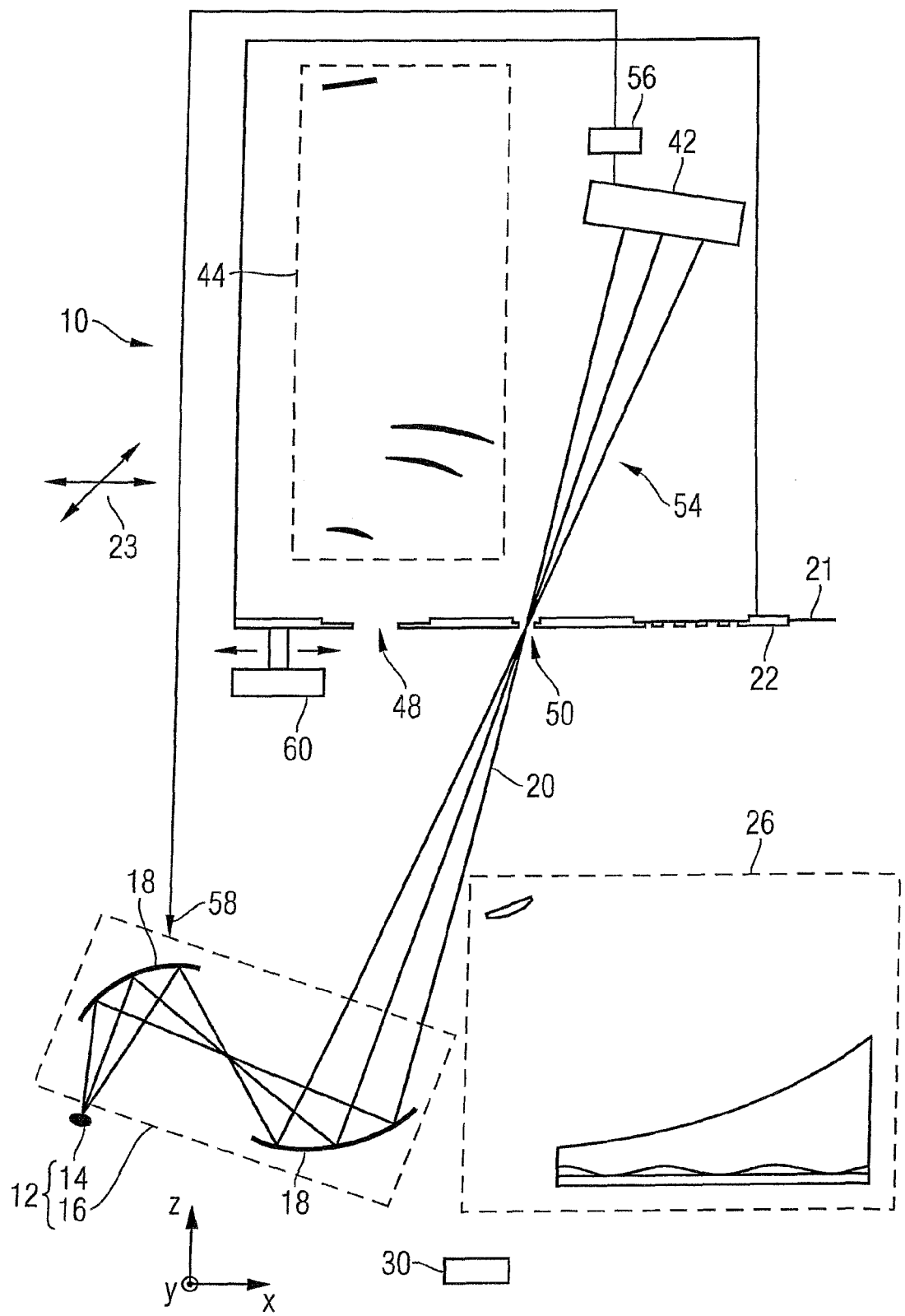
FIG. 3 shows the inspection apparatus as per FIG. 1 in a second measurement position for measuring an intensity distribution in a pupil of the illumination system.

In particular, the illustrated inspection apparatus 10 for inspecting a lithography mask serves to examine the lithography mask in respect of structural errors with regard to the mask structures arranged on the mask. To this end, the inspection apparatus 10 is operated in the inspection mode shown in FIG. 1. The subsequent FIGS. 2 and 3 show the inspection apparatus 10 in the measuring modes described in more detail below.

The inspection apparatus 10 comprises an illumination system 12, an object holder 22 in form of a displaceably mounted mask table, an inspection lens 26 and an inspection detector 30. The illumination system 12 comprises an EUV radiation source 14 and an illumination optical unit 16. The EUV radiation source 14 generates illumination radiation 20 in the EUV wavelength range, i.e. radiation with a wavelength of less than 100 nm, in particular with a wavelength of approximately 13.5 nm or approximately 6.8 nm. To this end, the EUV radiation source can for example comprise a pulsed discharge- and/or a laser plasma source.

The illumination radiation 20 passes through the illumination optical unit 16 and thereupon impinges on a surface 25 of the substrate 24 to be inspected, which is arranged in an illumination plane 21 of the illumination system 12. The illumination optical unit 16 is configured to radiate the illumination radiation 20 onto an illumination field in the illumination plane with intensity that is as uniform as possible and, as a result, irradiates the substrate 24 two-dimensionally. The illumination field has an extent that is greater than the quotient of the wavelength of the illumination radiation 20 and the numerical aperture of the illumination system 12. In accordance with one exemplary embodiment of an EUV illumination system with a numerical aperture of 0.2, the illumination field dimensions are approximately 0.4 mm×0.4 mm. The angle of incidence of the illumination radiation 20 on the substrate 24 is approximately 8° with respect to the surface normal of the substrate 24. In the shown embodiment, the numerical aperture of the illumination optical unit 16 is 0.2.

Furthermore, the illumination radiation 20 is manipulated by the illumination optical unit 16 such that the radiation incident on the substrate 24 at the respective field points has a predetermined angular distribution, or, expressed more precisely, a predetermined angularly resolved intensity distribution. This angularly resolved intensity distribution corresponds to the intensity distribution, i.e. the spatially resolved intensity distribution, in a pupil of the illumination optical unit 16. Examples of such intensity distributions in the pupil of the illumination optical unit comprise Gaussian distributions, annular distributions, and quadrupole and dipole distributions. The illumination optical unit 16 comprises a plurality of mirrors 18, which are provided for shaping the beam.

The section of the surface 25 of the substrate 24 situated in the illumination field is imaged in magnifying fashion on the inspection detector 30 with the inspection lens 26. To this end, the inspection lens 26 can have a magnification factor of e.g. 850. The inspection lens 26 comprises a plurality of mirrors 26 for reflecting EUV radiation. In order to measure the whole surface 25, the substrate 24 is displaced step-by-step in the substrate plane, i.e. the xy-plane as per the coordinate system from FIG. 1, using the object holder 22, as illustrated by the double-headed arrow 23.

In addition to a holder for the substrate 24 to be inspected, the object holder 22 comprises a measuring device 40 for measuring illumination properties of the illumination system 12, in the form of a measuring head integrated into the object holder 22. Specifically, the measuring device 40 can measure the intensity distribution in the illumination plane 21 and the intensity distribution in the pupil of the illumination system 12. As already mentioned previously, the measurement of the intensity distribution in the illumination plane 21 is also referred to as "illumination uniformity measurement" in the jargon of the art. As likewise already mentioned previously, the intensity distribution in the pupil describes an angularly resolved intensity distribution in the illumination plane 21.

The object holder 22 is provided with a repositioning device 60. The latter serves to reposition the object holder 22 between the inspection position shown in FIG. 1, a first measurement position shown in FIG. 2 and a second measurement position shown in FIG. 3. This is brought about by displacing the object holder 22 transversely with respect to the direction of incidence of the illumination radiation 20, i.e. in the x-direction as per the coordinate system of the drawing.

The measuring device 40 comprises two passage openings for the illumination radiation 20 which are integrated into the object holder 22—more precisely, a first passage opening 48 for operation in the first measurement position and a second passage opening 50 for operation in the second measurement position.

As already mentioned above, the operation in the first measurement position is illustrated in FIG. 2. In this position, the illumination radiation 20 passes into the measuring device 40 through the first passage opening 48. In accordance with one embodiment, the passage opening 48 has the dimensions of the illumination field generated on the substrate 24 by the illumination radiation 20, i.e., for example, 0.4 mm×0.4 mm. As a result, in the measurement position as per FIG. 2, the illumination radiation 20 can enter the measuring device 40 with the whole beam cross section thereof. In the measuring device 40, the illumination radiation 20 passes through a first measurement beam path 52, which is routed through an imaging optical unit, in this case in the form of a magnifying optical unit 44, and ends on a spatially resolving intensity detector 42 in the form of a CCD detector.

The magnifying optical unit 44 serves to image the intensity distribution in the illumination plane 21 on the spatially resolving intensity detector 42 in magnified form. The magnification factor can have different configurations and is at least ten as per one embodiment. In the exemplary embodiment as per FIG. 2, the magnification factor is approximately 30. To this end, the magnifying optical unit 44 is equipped with four mirrors 46 for reflecting EUV radiation. As a result of the magnification, the intensity detector 42 is able to record, with great precision, the intensity distribution in the illumination plane 21. The recorded intensity distribution is evaluated by an evaluation unit 56 in respect of the homogeneity thereof, i.e. in respect of local intensity deviations from the mean value. In other words, an illumination uniformity measurement is effected in the first measurement position. On the basis of the uniformity measurement, the evaluation unit 56 transmits control signals 58 to the illumination system 12, as a result of which corrections are undertaken on the illumination system 12 for improving the homogeneity of the emitted illumination radiation 20. By way of example, this can be brought about by adjusting one or more mirrors 18 in the illumination optical unit 16.

During the operation in the second measurement position, shown in FIG. 3, the illumination radiation 20 is radiated onto the second passage opening 50 by the illumination system 12. As mentioned above, the second measurement position is engaged by repositioning the measuring device 40 using the repositioning device 60. When repositioning the measuring device from the first measurement position into the second measurement position, the imaging optical unit in form of the magnifying optical unit 44 is moved out of the optical path of the illumination radiation 20. The second passage opening 50 has significantly smaller dimensions compared to the first passage opening 48. More precisely, it is so small that merely the radiation from one measurement point in the illumination plane 21 enters the measuring device 40 but it is large enough that said opening 50 does not produce any significant diffractive effects in the passing-through radiation. Thus, the extent of the second passage opening 50 is significantly smaller than the illumination field of the illumination system 12, but greater than the quotient of the wavelength of the illumination radiation 20 and the numerical aperture by at least one order of magnitude. Thus, the second passage opening 50 can, for example, be configured as a pinhole with a circular cross section. By way of example, a diameter of approximately 10 μm for the pinhole is suitable for measuring an illumination system 12 with a numerical aperture of 0.2 and an operating wavelength of 13.5 nm.

After passing through the second passage opening 50, the illumination radiation 20 runs along a second measurement beam path 54. In the illustrated exemplary embodiment, said beam path is characterized by an undisturbed beam path between the passage opening 50 and the intensity detector 42 for the incident direction of the illumination radiation 28. In other words, the second measurement beam path 54 is configured to let the illumination radiation 28 passing through the passage opening 50 run toward the intensity detector 42 in an undisturbed fashion. As a result, the second measurement beam path 54 renders possible wave propagation of the illumination radiation 28 in the region between the second passage opening 50 and the intensity detector 42. Hence, an image of the pupil of the illumination system 12 is generated on the intensity detector 42. This image reproduces the angularly resolved intensity distribution of the illumination radiation 20 at the point of the second passage opening 50.

As a result, the configuration of the second measurement beam path 54 transforms the angularly resolved intensity distribution of the illumination radiation 28 at the point of the passage opening 50 into a spatially resolved intensity distribution on the intensity detector 42. Alternatively, the second measurement beam path 54 can also comprise a Fourier optical unit. Such a Fourier optical unit likewise serves to transform a radiation distribution from angular space into positional space.

The angularly resolved intensity distribution, and hence the pupil intensity distribution, is measured for different points of the illumination field. To this end, the object holder 22 is displaced step-by-step in the illumination plane 21, as indicated by the double-headed arrow 23. The respective pupil intensity distribution is recorded by the evaluation unit 56 and firstly compared to a desired pupil intensity distribution and secondly evaluated in respect of its uniformity from point to point of the illumination field. On the basis of this evaluation, the evaluation unit 56 sends control signals 58 to the illumination system 12 for undertaking corresponding corrections on the illumination system 12. Further, it is possible to integrate the angularly resolved intensity distributions, measured for the different points of the illumination field in the second measurement position, for each of the field points over the respective angular range, and determine therefrom an intensity distribution of the illumination field, i.e. the illumination uniformity.

The measuring device 40 provides a compact measuring head for combined measurement of illumination uniformity and pupil intensity distribution of the illumination system 12. In the process, the measuring device 40 makes do with only one intensity detector 42. To this end, the measuring device 40 has two measurement beam paths 52 and 54, wherein the intensity detector 42 is used for measurements with both measurement beam paths. As a result, the calibration effort is restricted to one intensity detector only. In accordance with one exemplary embodiment, the intensity detector 42 can also be arranged outside of an evacuated region of the inspection apparatus 10, as a result of which improved thermal stability can be achieved.

The above-described measuring device 40 can also be configured separately, i.e. independently of the inspection apparatus 10. Thus, such a measuring device 40 can be used, for example, for qualifying an illumination optical unit 16 prior to the installation thereof into an inspection apparatus.

LIST OF REFERENCE SIGNS

10 Inspection apparatus
12 Illumination system
14 EUV radiation source
16 Illumination optical unit
18 Mirror
20 Illumination radiation
21 Illumination plane
22 Object holder
23 Double-headed arrow
24 Substrate to be inspected
25 Surface
26 Inspection lens
28 Mirror
30 Inspection detector
40 Measuring device
42 Spatially resolving intensity detector
44 Magnifying optical unit
46 Mirror
48 First passage opening
50 Second passage opening
52 First measurement beam path
54 Second measurement beam path
56 Evaluation unit
58 Control signal
60 Repositioning device

The invention claimed is:

1. A measuring device for measuring an illumination property of an illumination system, which is configured for two-dimensional irradiation of a substrate, arranged in an illumination plane, with illumination radiation, comprising:
a spatially resolving intensity detector,
two differing measurement beam paths formed in the measuring device, each of which is arranged to guide the illumination radiation emitted by the illumination system onto the intensity detector, wherein a first one of the measurement beam paths is arranged to measure an intensity distribution in the illumination plane and the second one of the measurement beam paths is arranged to measure an intensity distribution in a pupil of the illumination system, and
an imaging optical unit arranged in the first measurement beam path such that the illumination radiation guided in the first measurement beam path passes through the imaging optical unit.

2. The measuring device according to claim 1,
further comprising two passage openings arranged to respectively guide the two differing measurement beam paths to the intensity detector.

3. The measuring device according to claim 2,
wherein the passage opening associated with the first measurement beam path is larger than the passage opening associated with the second beam path.

4. The measuring device according to claim 2,
wherein the illumination system has a predetermined numerical aperture and emits illumination radiation having a predetermined wavelength, wherein the passage opening associated with the second measurement beam path is at least ten times larger than a quotient of the predetermined wavelength and the predetermined aperture.

5. The measuring device according to claim 1,
wherein the second measurement beam path is configured to enable wave propagation of the illumination radiation in a region between a passage opening and the intensity detector.

6. The measuring device according to claim 1,
wherein the second measurement beam path comprises a Fourier optical unit.

7. The measuring device according to claim 1,
wherein the imaging optical unit is configured as a magnifying optical unit with a magnification factor of at least ten.

8. The measuring device according to claim 1,
which is configured to measure illumination radiation in the EUV wavelength range.

9. An arrangement with a measuring device according to claim 1 and with a repositioning device, which is configured to reposition the measuring device with respect to the illumination system such that the illumination radiation enters either the first measurement beam path or the second measurement beam path.

10. An inspection apparatus for inspecting a surface of a substrate for microlithography, comprising an illumination system for two-dimensional irradiation of the substrate with illumination radiation and comprising a measuring device according to claim 1.

11. The inspection apparatus according to claim 10, which comprises an object holder for holding the substrate to be inspected, wherein the measuring device is arranged on the object holder.

12. The inspection apparatus according to claim 11, wherein the object holder is displaceably mounted between a first measurement position, in which the illumination radiation enters the first measurement beam path, and a second measurement position, in which the illumination radiation enters the second measurement beam path.

13. The inspection apparatus according to claim 10, wherein the illumination system comprises an extreme ultraviolet radiation source.

14. A method for measuring an illumination property of an illumination system, which is configured for two-dimensional irradiation of a substrate, arranged in an illumination plane, with illumination radiation, comprising:
  imaging a first intensity distribution of the illumination radiation in the illumination plane by guiding the illumination radiation in a first beam path that extends through an imaging optical unit and that impinges onto a spatially resolving intensity detector, and recording the imaged first intensity distribution,
  guiding the illumination radiation, in a second beam path that differs from the first beam path, that extends entirely outside the imaging optical unit, and that impinges onto the intensity detector, and recording a second intensity distribution of the illumination radiation in the illumination plane, such that an image of a pupil of the illumination system is generated on the intensity detector.

15. The method according to claim 14, wherein the method is performed using a single measuring device, which contains the imaging optical unit and the intensity detector.

* * * * *